US005777189A

United States Patent [19]

Alexanyan et al.

[11] Patent Number: 5,777,189
[45] Date of Patent: Jul. 7, 1998

[54] PROCESS FOR THE ALKYLATION OF OLEFINS

[75] Inventors: Georgy G. Alexanyan; Nikolay B. Librovitch, both of Moscow; Yuri A. Prochukhane, UFA, all of Russian Federation

[73] Assignee: Orgral International Technologies Corporation, St. Michael, Barbados

[21] Appl. No.: 450,615

[22] Filed: May 25, 1995

Related U.S. Application Data

[62] Division of Ser. No. 101,302, Aug. 3, 1993, Pat. No. 5,443,799.

[51] Int. Cl.$^6$ .................. C07C 2/56; C07C 2/58; C07C 2/62
[52] U.S. Cl. .......... 585/709; 585/711; 585/714; 585/716; 585/717; 585/720; 585/730
[58] Field of Search .................. 585/709, 711, 585/714, 716, 717, 720, 721, 730

[56] References Cited

U.S. PATENT DOCUMENTS

| | | |
|---|---|---|
| 881,434 | 3/1908 | Moburg. |
| 1,285,824 | 11/1918 | Snelling. |
| 1,371,205 | 3/1921 | Nashlund. |
| 2,014,212 | 9/1935 | Seguy. |
| 2,420,999 | 5/1947 | Ayers. |
| 2,440,423 | 4/1948 | Wiegand et al. |
| 2,664,450 | 12/1953 | Sachsse et al. |
| 2,747,974 | 5/1956 | Felger. |
| 2,976,127 | 3/1961 | Latham, Jr. |
| 2,981,747 | 4/1961 | Lang et al. |
| 3,000,994 | 9/1961 | Watson. |
| 3,006,739 | 10/1961 | Van Pool. |
| 3,098,108 | 7/1963 | Preiser. |
| 3,133,128 | 5/1964 | McDonald. |
| 3,220,803 | 11/1965 | Billi. |
| 3,227,774 | 1/1966 | Goldsby. |
| 3,238,021 | 3/1966 | Webber et al. |
| 3,311,452 | 3/1967 | Goodgame et al. |
| 3,438,741 | 4/1969 | Boyd et al. |
| 3,460,915 | 8/1969 | Lehrer et al. |
| 3,512,219 | 5/1970 | Stern et al. |
| 3,544,652 | 12/1970 | van Dijk. |
| 3,655,343 | 4/1972 | Galeano. |
| 3,696,168 | 10/1972 | Vanderveen. |
| 3,716,343 | 2/1973 | Chapman ............... 422/215 |
| 3,758,613 | 9/1973 | Anderson ............... 585/711 |
| 3,818,938 | 6/1974 | Carson. |
| 3,859,367 | 1/1975 | Yamamoto et al. |
| 3,867,103 | 2/1975 | Boney et al. |
| 3,925,502 | 12/1975 | Boney et al. ............ 585/720 |
| 3,956,417 | 5/1976 | Franz et al. |
| 4,017,263 | 4/1977 | Holmes et al. |
| 4,134,734 | 1/1979 | Winter, III. |
| 4,243,633 | 1/1981 | Hozuma et al. |
| 4,246,236 | 1/1981 | Di Gioacchino et al. |
| 4,276,439 | 6/1981 | Hutson, Jr. et al. ............ 585/720 |
| 4,289,732 | 9/1981 | Bauer et al. |
| 4,426,544 | 1/1984 | Carson ............... 585/709 |
| 4,590,044 | 5/1986 | Mos et al. |
| 4,752,452 | 6/1988 | Harbolt et al. |
| 5,037,616 | 8/1991 | Williatte et al. |
| 5,095,168 | 3/1992 | Kranz. |
| 5,292,986 | 3/1994 | Abbott ............... 585/730 |

FOREIGN PATENT DOCUMENTS

| | | |
|---|---|---|
| 446901 | 2/1948 | Canada. |
| 707226 | 4/1965 | Canada. |
| 1018452 | 10/1977 | Canada. |
| 1 255 877 | 6/1989 | Canada. |
| 2017123 | 11/1990 | Canada. |
| 2058430 | 10/1991 | Canada. |
| 2052150 | 3/1992 | Canada. |
| 2036174 | 8/1992 | Canada. |
| 1217303 | 5/1960 | France. |
| 856534 | 8/1981 | U.S.S.R. |
| 1452071 | 6/1988 | U.S.S.R. |
| 1459186 | 11/1988 | U.S.S.R. |
| 1519161 | 3/1989 | U.S.S.R. |

Primary Examiner—Elizabeth D. Wood
Attorney, Agent, or Firm—Foley & Lardner

[57] ABSTRACT

Disclosed is a process for the alkylation of an olefin with an isoparaffin using sulphuric acid as a catalyst. In this process, a finely-dispersed emulsion of isoparaffin and sulphuric acid is prepared first, in a separate emulsion preparation zone. This preparation is carried out by injecting the isoparaffin into the acid through a set of nozzles, thereby allowing the isoparaffin to "scavenge" at high speed through the acid and thus to form an extremely homogeneous emulsion. This makes it possible to achieve proper mixing without need of impellers or other similar mixing devices that usually call for substantial maintenance and operating costs. Then, the emulsion that was so prepared and which forms an already "finished" phase per se, is fed into a reaction zone which is separate from the emulsion preparation zone and in which the olefin is injected preferably at a plurality of points and in directions perpendicular to the emulsion flow. Advantageously, such an injection can be controlled so that the volume ratio of sulphuric acid to hydrocarbons present within the reaction zone is as low as from 0.3 to 0.5:1. This process allows reduction in the rate of expenditure of the raw materials, especially sulphuric acid, through the way and ratios at which the materials are mixed, and through analysis of the alkylation reaction process. An optimized, small-size, high-capacity and ecologically-clean apparatus for carrying out this process is also disclosed.

8 Claims, 4 Drawing Sheets

PROCESS FOR THE ALKYLATION OF OLEFINS

This application is a division of application Ser. No. 08/101,302, filed Aug. 3, 1993 and now U.S. Pat. No. 5,443,799.

BACKGROUND OF THE INVENTION a) Field of the Invention

The present invention relates to a process for the alkylation of olefins, and more particularly to a process wherein the alkylation of an olefin with an isoparaffin is carried out using sulphuric acid as a catalyst.

The invention also relates to an apparatus for mixing and reacting at least two and preferably three liquid compounds, which is particularly well adapted for carrying out the above process although it can also be used for carrying out numerous other processes, as will be explained hereinafter.

b) Brief Description of the Prior Art

Alkylation is a well-known process that is currently used in the petroleum industry to produce high-octane motor fuels by the combination of olefins (like propylene, butylene or amylene) with isoparaffins (essentially isobutane). This process is usually conducted in a liquid phase. Either sulphuric acid or hydrofluoric acid is used as a catalyst.

As aforesaid, the process according to the invention is essentially concerned with a process for the alkylation of olefins wherein sulphuric acid is used as catalyst.

So far, sulphuric acid alkylation has been suffering from a lack of quality and reliability of both the equipment layouts and the working conditions, including in particular the rate of reaction. Alkylation plants employing sulphuric acid as a catalyst often operate with an isoparaffin-to-olefin volume ratio in the range of 5:1 to 8:1 and a sulphuric acid-to-hydrocarbons volume ratio of about 1:1.5.

In the existing plants, the average consumption of acid per metric ton of alkylate is about 80 kg.

Among the processes that are presently known, one may distinguish between those where:

1—the olefin, isoparaffin and sulphuric acid are fed separately into a reactor in which they are contacted generally under vigorous agitation to form a reactive emulsion (see for example, U.S. Pat. No. 3,227,774 and USSR Author's certificate Nos. 1,452,071 and 1,459,186);

2—the olefin and isoparaffin are mixed together first and the resulting mixture is fed or injected into an alkylation reactor containing an emulsion of sulphuric acid and hydrocarbons (see, for example, U.S. Pat. Nos. 3,867,103; 3,956,417 and 5,095,168);

3—the olefin and sulphuric acid are mixed together first in order to prepare the corresponding alkyl sulphate that is then fed together with the isoparaffin into a reactor (see, for examples, U.S. Pat. No. 3,000,994 and Canadian patent No. 446,901); and 4—the isoparaffin and sulphuric acid are mixed together to form an emulsion and this emulsion is then reacted with the olefin (see, for example, U.S. Pat. No. 3,544,652 and USSR Author's certificate No. 1,519,161).

The process according to the invention is of the fourth type mentioned hereinabove, i.e. of the type wherein the isoparaffin and sulphuric acid are mixed first to form an emulsion prior to being contacted with the olefin.

In the closest prior art reference known to the instant Applicant, namely USSR Author's certificate No. 1,519,161 issued on Jul. 1, 1989 with designation of two of the three inventors of the present invention, there is disclosed a process for carrying out the alkylation of an isoolefin with an isoparaffin in the presence of sulphuric acid, wherein the isoparaffin-to-isoolefin volume ratio is ranging from 5:1 to 6:1 and the sulphuric acid-to-hydrocarbons volume ratio from 0.5:1 to 0.8:1.

In this process, sulphuric acid is mixed with isoparaffin in one part of a cylindrical apparatus to form an emulsion that is subsequently fed into a directly adjacent part of the cylindrical apparatus at a flow rate of 20 to 25 m/s. The isoolefin at a temperature of −21.4° C. to −7.6° C. is fed at a flow rate of 15 to 20 m/s. The process is carried out with the mixture moving in the apparatus at a flow rate of 11.7 to 15 m/s.

The apparatus used for carrying out the process disclosed in this Author's Certificate No. 1,519,161 comprises a cylindrical casing that is provided with plate-shaped thermostating elements. The casing has pipe connections through which the acid, isoparaffin and isoolefin are fed. First, an emulsion of sulphuric acid and isoparaffin is prepared at one end of the cylindrical casing. The isoparaffin is fed through a cylindrical pipe provided with holes at right angles to the acid flow. The emulsion that is so prepared is then mixed up with the isoolefin at the other end of the cylindrical casing. The isoolefin cooled to −7.4° C. to −21.4° C. is fed through a tapered portion of the casing thereby making it additionally turbulized. The reactive mass remains in contact for 5 to 10 seconds and then moves to an adjacent settling tank. The heat liberated during the reaction is controlled by the low temperature of the isoolefin and is evenly distributed by means of the thermostating plates.

In the process described in USSR Author's Certificate No. 1,519,161, no separate and distinct zones are provided for the emulsion preparation and the ajacent reaction, the whole process taking place within a single cylindrical casing with the isoparaffin and acid coming in at one end and moving to the other end of the casing to enter into contact with the olefin. This apparatus does not allow for adiabatic expansion of the emulsion.

In the apparatus disclosed in USSR Author's Certificate No. 1,519,161, no means are provided to distribute the feed of isoolefin to the reactor. This results in local macroinhomogeneity, overheating in the isoolefin feeding area and appearance of unfavourable side-reactions (oligomerization, self-alkylation, olefin sulfonation, etc.). As a result, it becomes necessary:

1) to increase the isoparaffin-to-isoolefin volume ratio range to 5:1 to 6:1;

2) to increase the circulation of idle isobutane;

3) to decrease the absolute concentration of isoolefin; and 4) to increase the consumption of $H_2SO_4$.

In the same USSR Author's Certificate No. 1,519,161, removal of heat is carried out by cooling the olefin that is being fed and by controlling the temperature thermostatically by means of special plates. Such is not an effective means to remove heat. As a matter of fact, the method used in this Author's Certificate just allows for partial redistribution of the reaction heat. This method does not and cannot provide isothermic conditions.

In USSR Author's Certificate No. 1,519,161, no means are also provided to check the temperature of the sulphuric acid that is being fed. Accordingly, it is impossible to maintain an optimal emulsion formation process because the freezing point greatly depends on the sulphuric acid concentration (+10.3° C. for 100% $H_2SO_4$, −38° C. for 93.5% $H_2SO_4$ and +7.9° C. for 85% $H_2SO_4$—see A. G. Amelin.

Sulphuric acid process, Khimiya publishing house, Moscow-Leningrad, 1964, p. 439).

When the acid viscosity greatly changes, the dispersity of the emulsion that is being formed varies. Such a viscosity can be estimated by the empirical formula (Timmermans, Vol. 111, p. 1319):

$$3.63\xi = 374/(t+1.7^\circ\ C.-47)$$

where $\xi$ is the viscosity, cP;

t is the temperature, °C.;

C is the percentage of $H_2SO_4$;

a is the parameter depending on C (4.7 for 100-% $H_2SO_4$, 4.1 for 90-% $H_2SO_4$, 4.0 for 86-% $H_2SO_4$).

Thus, if the temperature increases from 0° to 25° C., the viscosity of the 95-% $H_2SO_4$ will decrease from 44.93 to 17.68 cP, the viscosity of the 90-% $H_2SO_4$ from 47.59 to 18.20 cP and the viscosity of the 98.5-% $H_2SO_4$ commonly used in the alkylation process will be such that the sulphuric acid is in a solid state at 0° C. Therefore, if the flow temperature cannot be accurately checked, it is impossible to check the parameters of the sulphuric acid—isobutane emulsion, which results in an overexpenditure of sulphuric acid, a decrease of the alkylate quality, and an improper operation of the apparatus.

In the apparatus disclosed in USSR Author's Certificate No. 1,519,161, no means are further provided to check the acidity of the sulphuric acid during the process. Once again, this may bring the process out of its optimal mode of operation if, for example, some foreign compounds or mixture get into the sulphuric acid, such as water that may appear due to an insufficient drying of the raw material (hydrocarbons). In this connection, it may be appreciated that a reduction of 1% in the acid concentration due to dilution with water reduces by 1.5 to 2 times the acidity of the catalyst and reduces by 2.5 to 4 times the alkylation reaction rate (see Industrial and Laboratory Alkylations, edited by L F. Albright and A. R. Goldsby, translated from English, Khimiya publishing house, Moscow, 1982, p. 101). In addition, such a reduction in the acidity of the catalyst may result in a premature catalyst failure, a sulphuric acid overexpenditure and an increased corrosion of the device.

Last of all, in the apparatus disclosed in USSR Author's Certificate No. 1,519,161, no means are provided to check the composition of the catalyst during the process, which, in turn, makes it impossible to observe variations of the concentration of the undissociated sulphuric acid that may be caused by the duration of catalyst use. This leads inevitably to unfavourable changes in the catalyst properties because of foreign compounds or mixtures penetration and/or formation in the catalyst after interaction with the raw material or after feed of fresh sulphuric acid. In addition, it is impossible to determine the parameters of the fresh and spent acids and to use promoters in the required amount.

In U.S. Pat. No. 3,544,652 issued on Dec. 1, 1970, there is disclosed a process for carrying out the alkylation of an olefin with an isoparaffin in the presence of sulphuric acid, where the isoparaffin-to-olefin volume ratio is preferably equal to 12:1 and the sulphuric acid-to-hydrocarbons volume ratio is ranging from 2.5:1 to 15:1 and is preferably controlled at 6:1.

In this process, the olefin is reacted with an acid alkylatable hydrocarbon emulsion which is formed by intimately mixing the isoparaffin with sulphuric acid prior to contact with the olefin. The reaction is carried out adiabatically and preferably under flood conditions in a reactor called "alkylation contactor", in which the olefin is injected at a high mixing rate from a plurality of feed points. The reactor is equipped with a mixing device suitable for forming and maintaining the emulsion of isoparaffin and sulphuric acid and for intimately and uniformly mixing the emulsion with the olefin at each site of olefin introduction.

The temperature of the alkylation mixture gradually increases by 5° to 15° C. in the direction of liquid flow, thereby reducing the viscosity of the mixture and facilitating flow and mixing.

The process disclosed in this U.S. patent is preferably carried out at temperatures ranging from 5° to 60° C. under a pressure sufficient to maintain the reactants in liquid phase (from 2 to 10 atmospheres). Use is made of 88 to 99% sulphuric acid cooled to about 4° C. prior to being mixed with the isoparaffin.

In this U.S. patent, very few details are given as to the way the emulsion is prepared and the olefin is injected and distributed into the reaction zone(s). The reaction heat is not removed and no reference is made to any control of the temperature, acidity and composition of the sulphuric acid within the reactor.

OBJECTS AND SUMMARY OF THE INVENTION

An object of the present invention is to provide a process for the alkylation of olefins, which is of the above mentioned "fourth" type, but is substantially improved as compared to the existing processes, including those previously discussed, inasmuch as:

it allows reduction in the rate of expenditure of the raw materials, especially sulphuric acid, through the way and ratios at which the materials are mixed, and through rapid analysis of the alkylation reaction process;

it improves the target product quality; and it uses an optimized, small-size, high-capacity, and ecologically-clean apparatus for carrying it out.

In accordance with the invention, this first object is achieved with a process for the sulphuric acid alkylation of at least one olefin with at least one isoparaffin, which comprises the steps of:

a) feeding sulphuric acid into an emulsion preparation zone;

b) injecting the isoparaffin(s) through a set of nozzles into the emulsion preparation zone in such a manner as to prepare, without any impeller or other mixing means, a homogeneous emulsion of the isoparaffin(s) sulphuric acid;

c) injecting the olefin(s) into the so-prepared emulsion in a reaction zone separate from the emulsion preparation zone so as to form a reaction mixture;

d) allowing the reaction mixture to react within the reaction zone and;

e) recovering from the so-reacted mixture.

When this process is used for preparing alkylates useful as motor fuel the olefin preferably consists of butylenes and the isoparaffin is essentially isobutane. Other isoparaffins such as isopentane may also be present, but are to be avoided since they are usually considered as components reducing the quality of the alkylate.

Thus, in the process according to the invention, a finely-dispersed emulsion of isoparaffin and sulphuric acid is prepared first, in a separate emulsion preparation zone. This preparation is carried out by injecting the isoparaffin into the acid through a set of nozzles, thereby allowing the isoparaffin to "scavenge" at high speed through the acid and thus to form an extremely homogeneous emulsion. This makes it possible to control step (a) of the process in such a manner that the volume ratio of sulphuric acid to hydrocarbons present within the reaction zone is as low as from 0.3:1 to 0.5:1, which is a substantial advantage. This also makes it possible to achieve proper mixing without need of impellers or other similar mixing devices that usually call for substantial maintenance and operating costs.

Then, the emulsion that was so prepared and which forms an already "finished" phase per se, is fed into a reaction zone which is separate from the emulsion preparation zone and in which the olefin is injected preferably at a plurality of points and in directions perpendicular to the emulsion flow. Advantageously, such an injection can be controlled so that the volume ratio of said at least one isoparaffin to said at least one olefin is higher than 2:1.

The use of "jet reactors", i.e. reactors in which one of the reactants is injected through a set of nozzles into another reactant is already known in the art.

Thus, for example, U.S. Pat. Nos. 3,133,128; 3,696,168 and 3,867,103 disclose reactors for the alkylation of olefins, in which a mixture of olefin and isoparaffin is injected through a set of nozzles into a bath of acid to form a reactive emulsion. However, none of these patents discloses or suggests even remotely to carry out the alkylation process in two separate zones, namely a first one where a highly homogeneous emulsion of isoparaffin and acid is prepared and a second one, downstream and separate from the first one, in which the olefin is injected into the emulsion.

It is worth mentioning that in both zones the reactants (i.e. the isoparaffin injected through the nozzles, the prepared emulsion entering the reaction zone and the olefin injected into the reaction zone) are subject to an adiabatic expansion which absorbs a substantial part of the reaction heat and thus allows the reaction to be carried out under a quasi-isothermal condition. To further control the reaction temperature, one may control the temperature of the isoparaffin injected into the emulsion preparation zone so that it ranges between $-10°$ and $+5°$ C.; the temperature of the sulphuric acid fed into the same emulsion preparation zone so that it ranges between $5°$ and $20°$ C., preferably $8°$ to $10°$ C., and the temperature of the olefin injected into the reaction zone so that it ranges between $-10°$ and $+5°$ C., preferably $0°$ C. Such a control can be achieved by external cooling of the raw material.

Thus, in the process according to the invention, the reaction is advantageously carried out in an isobaric-isothermal manner, thanks to:

the structure of the equipment that is divided into an emulsion preparation zone and a separate reaction zone;

the homogeneity both in quality and distribution, of the emulsion that is prepared; and a proper control of the temperature of the isoparaffin and/or sulphuric acid and/or olefin.

In accordance with a preferred embodiment of the invention, steps (a) and (b) are advantageously controlled so that the prepared emulsion moves within the emulsion preparation zone at a flow rate of 0.2 to 2 mls. In such a case, step (c) may be controlled so that the reaction mixture that is formed after injection of said at least one olefin moves within the reaction zone at a flow rate of 0.04 to 0.27 m/s. Depending on the selected flow rates contact between the reagents may last from a few seconds up to 60 seconds, thereby reducing to a minimum the side reactions such as the oligomerization of olefins and the self-alkylation of the isoparaffin.

In accordance with another preferred embodiment of the invention, the conditions of operation of the process according to the invention may also be substantially optimized by:

measuring the acidity function $H_o$ of the sulphuric acid within both the emulsion preparation zone and the reaction zone and controlling the quality of the sulphuric acid fed in step (a) and the temperature and pressure of the sulphuric acid, of the at least one isoparaffin and of the at least one olefin fed or injected in steps (a), (b) and (c) so that the acidity function $H_o$ ranges from $-10.6$ to $-9.5$; and/or measuring the concentration of undissociated sulphuric acid molecules within both the emulsion preparation zone and the reaction zone and controlling the quality of the sulphuric acid fed in step (a) and the temperature and pressure of the sulphuric acid, of the at least one isoparaffin and of the at least one olefin fed or injected in steps (a), (b) and (c) so that the concentration ranges from 6.8 to 16.9 g mol/l.

As will be better explained hereinafter, the process according to the invention as defined hereinabove has been tested.

During these tests, the average consumption of sulphuric acid per metric ton of produced alkylate has been ranging between 30 to 40 kg, which is much smaller than in the existing plants.

The process has proved to be very efficient and ecologically safe for producing alkylate using sulphuric acid as a catalyst. The wastes are significantly reduced. The surface area of the production site and the labor consumption are also both reduced. The equipment to carry the process out is hermetically sealed.

The tests have further demonstrated that the process according to the invention allows for the formation of a light, unstable emulsion. The separation of the reacted mixture into hydrocarbon and acid phases takes place in 5 to 8 seconds, thereby allowing the settling time to be reduced.

As the process according to the invention does not need any impellers or other mixing means subject to substantive corrosion, the equipment used to carry out the process according to the invention is easy to maintain and service. The equipment can be hermetically sealed and is advantageously operated at a low pressure of 1 to 7.5 surplus atmospheres, preferably 1.5 surplus atmospheres in the reation zone, thereby providing stable hydrodynamics. This equipment is also compact in size and its reliability in use allows the process to reach its normal work regime within 5 to 7 minutes, as compared to 20 to 30 minutes with the traditional methods.

The process according to the invention, thanks to the way it is carried out, can easily be subject to automation.

As explained hereinabove, a unique and original set of express-control steps was developed to monitor the parameters of the process and maintain the optimum operationa conditions. This set of express-control steps was developed on the basis of changing physical and chemical parameter: of the catalyst during the process. The acidity function $H_c$ and the non-dissociated sulphuric acid content in the catalys are the basic physical and chemical parameters of the catalyst (sulphuric acid).

In accordance with the invention, both of these values car be measured during the process at 1 to 10 minute interval: with a plus or minus five percent (5%) accuracy, whicl allows to control the production process. Such a measure ment of the acidity function $H_o$, which is the negative logarithm of the acidity $h_o$ of the acid solution, can be carried out by measuring the rate of formation of carbor oxide (CO) after addition of a given amount of a carboxylic acid into a sample of sulphuric acid from the tank or reactor. As the rate of decomposition of carboxylic acids such as formic acid is in direct proportion to the acidity of the reaction medium, one can easily infer from the rate of formation of CO, the acidity of the sample and thus the acidity function $H_o$ of the catalyst.

This process and the characteristics of the apparatus allow for rapid modifications of parameters such as pressure and temperature of incoming components so as to rapidly adjust these parameters with the changing properties of the catalyst. As an example, in alkylation of olefins the properties of the acid which is fed such as viscosity, freezing point and others are modified as it reacts with the components; for the first time this process allows for almost immediate modifications to the parameters of the incoming flows of olefins, isoparaffins and acid in order to achieve very rapidly the optimum regime inside the reactor.

Thus, in short, with (1) an increased specific productivity and a more rational use of the inputs. (2) a reduction in the consumption and waste of energy; and (3) a reduction of acid consumption, the process according to the invention permits to dramatically reduce alkylate production costs while increasing the production volume.

The absence of impellers and the hermetical sealing of the equipment used to carry it out also permits the process to operate at low pressures with ecological purity, thereby making it environmentally safer.

Another object of the present invention is to provide an apparatus especially adapted for carrying out the above process, although it could be used for carrying out numerous other processes where two or three liquid compounds are to be thoroughly mixed and reacted.

In accordance with the invention, this other object is achieved with an apparatus comprising:

a) a generally cylindrical tank having a longitudinal axis, a given length $l_1$ and a given diameter D1, this tank defining an emulsion preparation zone being provided at one end with a centrally positioned, axially oriented outlet opening of a diameter D6 smaller than D1;

b) means for injecting into the tank, a first compound to be mixed and reacted, the injecting means comprising a plurality of nozzles of average diameter D2 located within the tank opposite the outlet opening, the nozzles extending into the emulsion preparation zone in a direction generally parallel to the longitudinal axis of the tank over a length $l_2$;

c) means for radially feeding into the tank a second compound to be mixed and reacted; and d) a generally cylindrical reactor vessel (hereinafter called "reactor") having a longitudinal axis aligned with the axis of the tank, a given length $l_5$ and a given diameter D4 larger than D1, this reactor defining a reaction zone separate and downstream from the emulsion preparation zone and having an inlet conduit of diameter D6 that is centrally positioned and axially oriented at one end thereof and in direct communication with the outlet opening of the tank, and, opposite this inlet, a discharge opening that is centrally positioned and axially oriented.

Preferably, the injecting means (b) comprises a perforated plate extending transversely within the tank upstream of the feeding means (c) and a first branch pipe opening into the tank upstream of the perforated plate. The first compound is fed into the tank through this first branch pipe and injected into the emulsion preparation zone through the nozzles of length $l_2$ that project from the plate toward the outlet of the tank.

Preferably also, the feeding means (c) comprises a distribution chamber in the form of a sleeve surrounding the tank. This distribution chamber is in direct communication with the tank through an annular radial opening made within the tank close to the perforated plate downstream of the same. A second branch pipe of diameter D3 is used to feed the second compound to be reacted into the distribution chamber. This second branch pipe opens into the distribution chamber at a distance $l_3$ away from the radial opening.

This basic apparatus can be used for intimately mixing two compounds together in view of making them react.

Thus, for example, the apparatus can be used for the polymerization of α-olefins. In this polymerization process, the catalyst which is preferably a liquid mixture of $AlCl_3$, can be fed through the first branch pipe and nozzles whereas the raw material to be polymerized, i.e. a mixture of olefins and hydrocarbons, is fed through the second branch pipe and distribution chamber. The polymerization reaction occurs within the emulsion-preparation tank in which the catalyst and raw material are fed, while the reactor downstream of the tank acts as a reaction temperature control chamber to avoid overheating.

In this polymerization process, the molecular mass of the obtained product can be regulated by proper adjustment of the pressure inside the apparatus. An increase in pressure within the apparatus will result in an increase in temperature and in a reduction in the molecular mass of the reaction product.

In this manner, the molecular mass of the reaction product can be easily adjusted between 300 to 10,000 and the conversion of α-olefin can be up to 100%.

The apparatus according to the invention can also be used for the production of butyl rubber and synthetic rubbers. In such a case, the rubber monomer could be fed through the second branch pipe while the Zigler-Natta catalyst and optional stoppers and regulators are injected through the first branch pipe and nozzles.

The same apparatus could further be used for:

the production of synthetic boiled oil, by feeding piperylene through the second branch pipe while injecting an accelerator such as $AlCl_3$ through the nozzles;

the reaction of a butane-containing mixture with sulphuric acid in the production of methyl-ethyl-ketone for use as a solvent for lacquers and dyes and as a raw material in the refinery industry;

the oxidation of heavy hydrocarbons in the production of construction and road bitumen;

the preparation of Zigler-Natta catalysts;

the hydrolysis of complex esters, using sulphuric acid as a catalyst;

the nitration of aromatic compounds, using a nitrating mixture of sulphuric and nitric acids;

the sulphonation of aromatic and heterocyclic compounds, using sulphuric acid as both a reagent and a catalyst;

etc. . . .

When the reaction to be carried out involves a third compound to be mixed and reacted, like in the case of the alkylation of an olefin, the apparatus according to the invention as defined hereinabove may further comprise (e) means for radially feeding into the reactor the third compound to be mixed and reacted.

This means (e) advantageously comprises a feeding pipe of diameter D5 extending centrally and axially over a length $l_6$ within the reactor. This pipe has a feeding end extending out of the reactor, through which the third compound is fed.

It also has a closed end stopping at a short distance $l_7$ from the inlet of the reactor, and a plurality preferably more than 10 of radial openings of diameter $d_6$ uniformly distributed along all its length.

Preferably, the closed end of the feeding pipe is cone-shaped and has an apex of 45° to 60° facing the inlet of the reactor.

When the apparatus according to the invention is used for the alkylation of olefins, an isoparaffin, such as, for example, isobutane, may be fed through the first branch pipe and injected into the tank through the nozzles. Simultaneously, sulphuric acid may be fed through the second branch pipe and the distribution chamber into the tank. This permits to prepare a homogeneous emulsion of sulphuric acid and isobutane. This emulsion then enters the reactor, in which the olefin to be reacted is injected through the feeding pipe.

It is worth mentioning that the apparatus provided with a pipe for feeding into the reactor a third compound to be reacted, can also be used to carry out other reactions involving three compounds. Thus, for example, it could be used to prepare chloride-substituted hydrocarbons such as $CH_3Cl$ or $C_2H_4C_2$, chloride-substituted aromatic compounds or chloride rubber, by injecting $AlCl_3$ or $FeCl_3$ used as a catalyst through the nozzles into a hydrocarbon, an aromatic compound or a rubber monomer fed through the second branch pipe while chloride in an inert solvent is fed into the reactor through the feeding pipe.

In accordance with a preferred embodiment of the invention, the dimensions of the different structural components of the apparatus according to the invention are selected so that:

the ratio D1/D2 ranges from 9.5:1 to 24:1 the ratio D1/D6 ranges from about 2:1 to 2.3:1, preferably 2:1 the ratio D1/D4 ranges from 1:2 to 1:4 the ratio D4/D5 ranges from 8:1 to 16:1 the ratio $l_1/l_2$ ranges from 3.3:1 to 5:1 the ratio $l_1/l_5$ ranges from 1:2 to 1:3 the ratio $l_5/l_6$ ranges from 1.1:1 to 1.3:1 the ratio $l_7$ ranges from 2 to 6 times D5;

the ratio $l_3$/D3 ranges from 3:1 to 1:1, preferably 2:1 to 1:1;

the ratio $d_6$/D5 ranges from 1:6 to 1:10.

The distance between the outlet of the tank and the inlet of the reactor may be selected so that the ratio $l_1/l_4$ ranges from 1.1:1 to 2.1:1.

Preferably also, the sum of the cross-section areas of the nozzles are selected to be equal to the cross-section area of the second branch pipe, and the nozzles are spaced apart from each other at a distance lower than twice their diameter D2.

In practice, the total length of the apparatus may be, for example, equal to about 5 meters and the diameter D4 of the reactor may be equal to about 0.6 meters. In such a case, the weight of the apparatus may be of about 1,200 kg. With such an apparatus whose other structural dimensions can be easily determined with the above ratios, more than 150 metric tons of alkylate per day may be produced. By proper selection of the above ratios, up to 450 metric tons of alkylate per day may be produced.

BRIEF DESCRIPTION OF THE DRAWINGS

The process according to the invention and the way it may be carried out, will be better understood upon reading the following non-restrictive description given with reference to the accompanying drawings in which.

DESCRIPTION OF A PREFERRED EMBODIMENT

Figure 1:
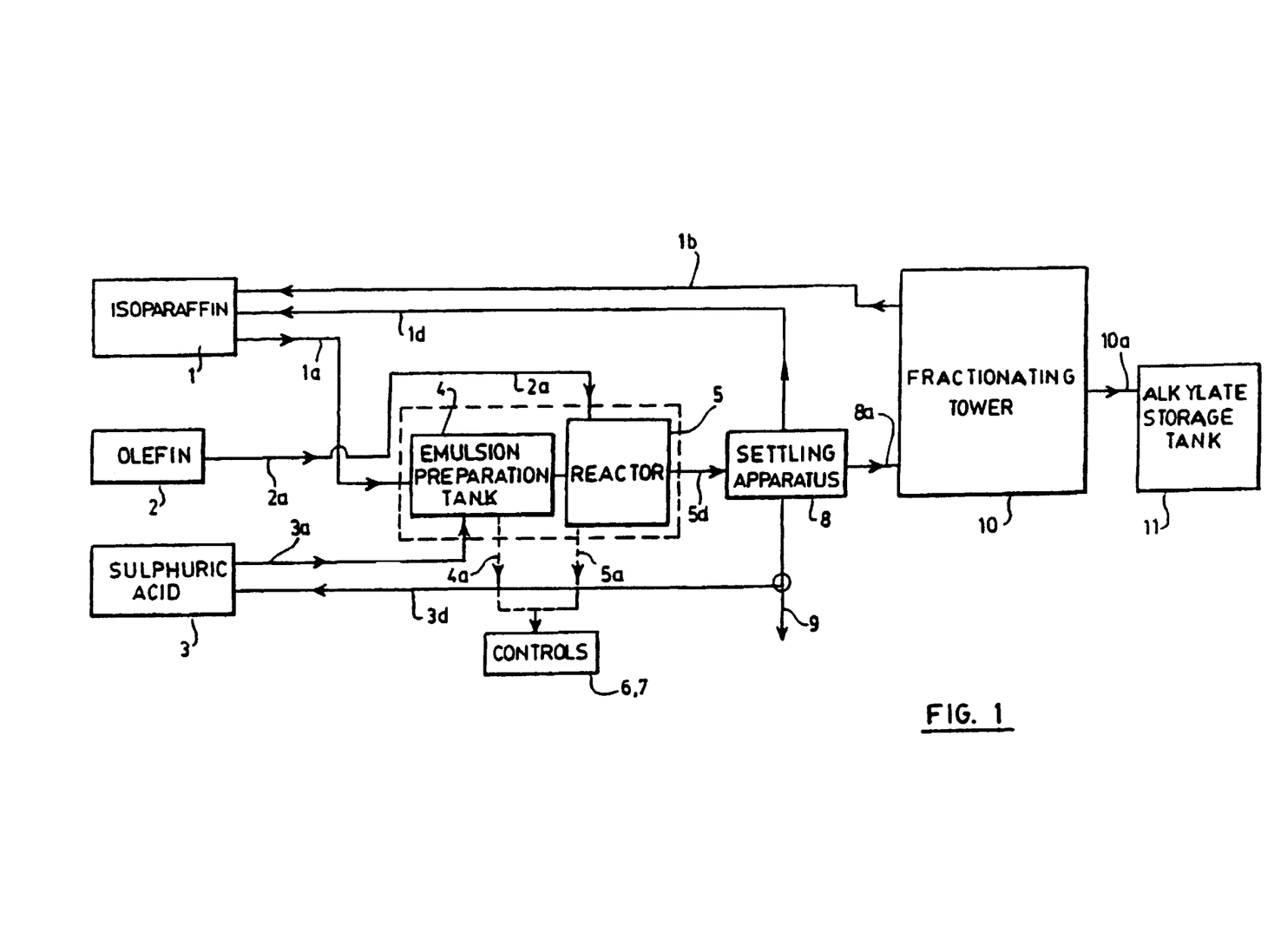
FIG. 1 is a flow chart of an alkylation plant incorporating an apparatus according to the invention.

As aforesaid, FIG. 1 is a flow chart of an alkylation plant incorporating an apparatus according to the invention.

As can be seen, in this plant, the isoparaffin which is preferably isobutane and the catalyst which is sulphuric acid, are fed from tanks 1 and 3 through pipelines 1-a and 3-a, into an isobutane-sulphuric acid emulsion preparation tank 4. The emulsion prepared within the tank 4 is delivered to a reactor 5 in which it is mixed with the olefin, which can be isobutylene or a mixture containing it. This olefin is supplied from a tank 2 though a pipeline 2-a. Upon completion of the reaction, the emulsion is delivered through a pipeline 5-d to a settling apparatus 8, from which the hydrocarbon phase is fed to a fractionating tower 10 through a pipeline 8-a. Isobutane evolving by boiling in the reactor 5 is returned to the tank 1 through the settling apparatus 8 and pipeline 1-d. The catalyst (sulphuric acid) settled within the apparatus 8 is returned through a pipeline 3-d to the tank 3. The used acid can be disposed through a discharge outlet 9. Isobutane liberated during the fractionating process in the tower 10 is returned to the tank 1 through the pipeline 1-b and the alkylate fed to a storage tank 11 through a pipeline 10-a. During the process which is continuous, samples of the reaction mixture are taken on trial from the isobutane-sulphuric acid emulsion preparation tank 4 and from the reactor 5 by a sampling system through manifolds 4-a and 5-a. These samples are fed to a device 6 for making acidity analysis and to a device 7 for making the measurement of the composition of the alkylation acid phase (catalyst).

As aforesaid, the invention lies in the apparatus used for carrying out the alkylation reaction within the plant, and in the process that is carried out within this apparatus whose main components are:

the isobutane-sulphuric acid emulsion preparation tank 4; and the separate reactor 5 in which the olefin is injected.

Figure 2:
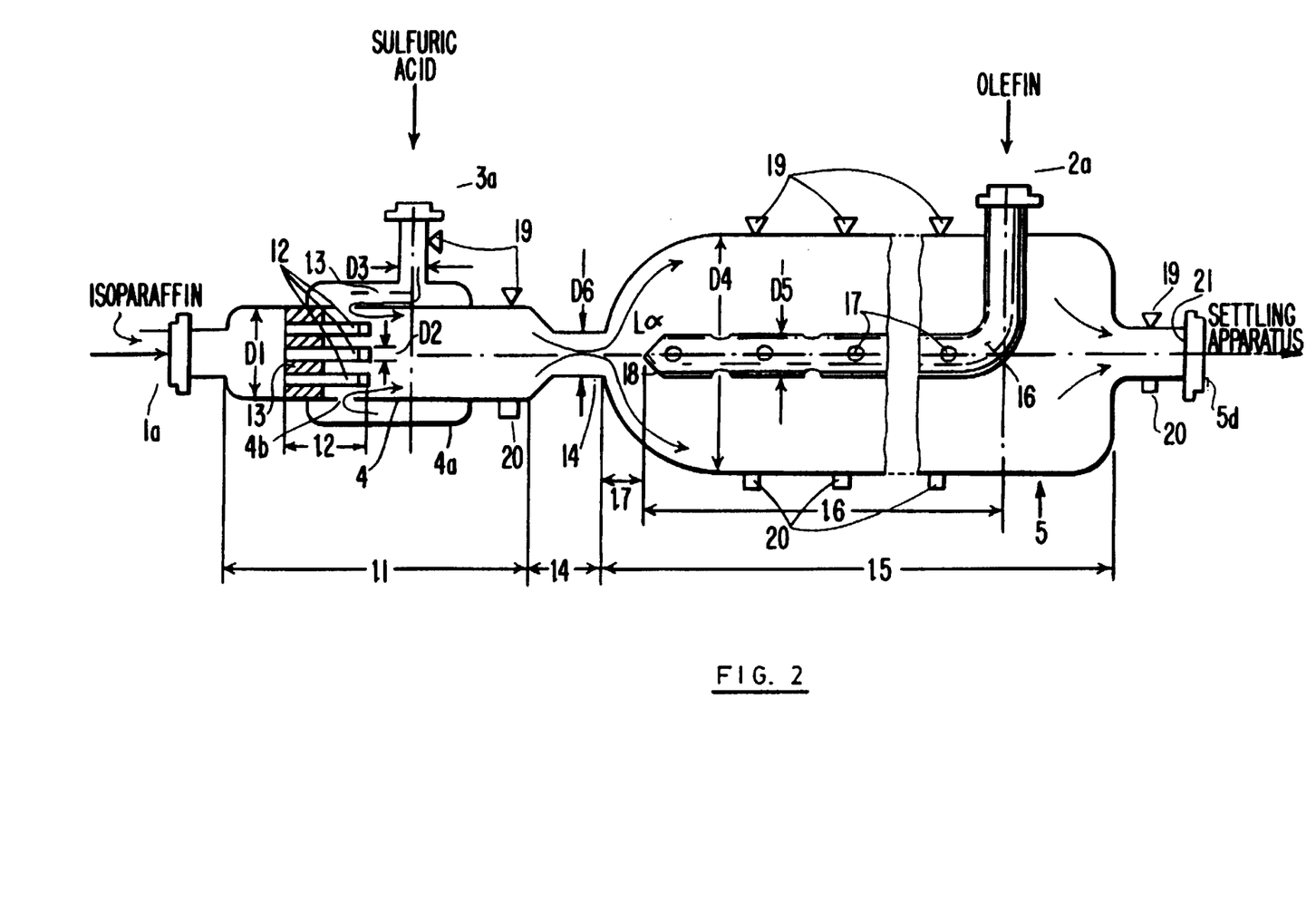
FIG. 2 is a schematic, cross-sectional view of the apparatus according to the invention, as it is used in the alkylation process illustrated in FIG. 1.
Figure 3:
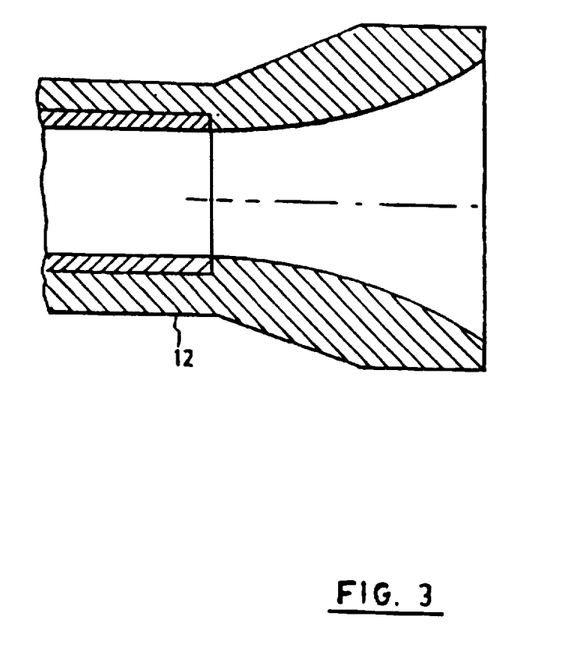
FIG. 3 is a cross-sectional view of an injection nozzle of the apparatus shown in FIG. 2.

As is better shown in FIG. 2, the emulsion preparation tank 4 is generally cylindrical and has a longitudinal axis, a given length $l_1$ and a given diameter D1. This tank 4 is provided at one end with a centrally positioned, axially oriented outlet 14 in the form of a branch pipe of a length $l_4$ and a diameter D6 smaller than D1.

Means are provided for injecting the isoparaffin into the tank 4. These means comprise a perforated plate 13 extending transversally within the tank 4 adjacent the end of it that is opposite to the outlet 14. They also comprise a set of axially oriented nozzles 12 of length $l_2$ and outer diameter D2 that project from the perforated plate 13 toward the outlet 14 of the tank. The injecting means further comprise a first branch pipe which is connected to the pipeline 1-a. This first branch pipe opens into the tank upstream of the perforated plate 13.

Means are also provided for radially feeding the sulphuric acid into the tank 4 so that it is "scavenged" by the isoparaffin fed through the pipeline 1-$a$ and nozzles 12 to form an emulsion.

As is shown, these feeding means comprise a distribution chamber in the form of a sleeve surrounding the tank 4, which is in direct communication with the tank through an annular radial opening made within the tank 4 close to the perforated plate 13 downstream of the same. The feeding means also comprise a second branch pipe of diameter D3 which is connected to the pipeline 3-$a$. This second branch pipe opens into the distribution chamber at a distance $l_3$ away from the radial opening.

As aforesaid, the tank 4 is in communication with the reactor 5. This reactor 5 is generally cylindrical and has a longitudinal axis aligned with the axis of the tank, a given length $l_5$ and a given diameter D4 larger than D1. It also has an inlet of diameter D6 that is centrally positioned and axially oriented at one end thereof and in direct communication with the outlet 14 of the tank. The reactor 5 further has, opposite its inlet, a discharge 21 in the form of a branch pipe that is centrally positioned and axially oriented.

Figure 5:
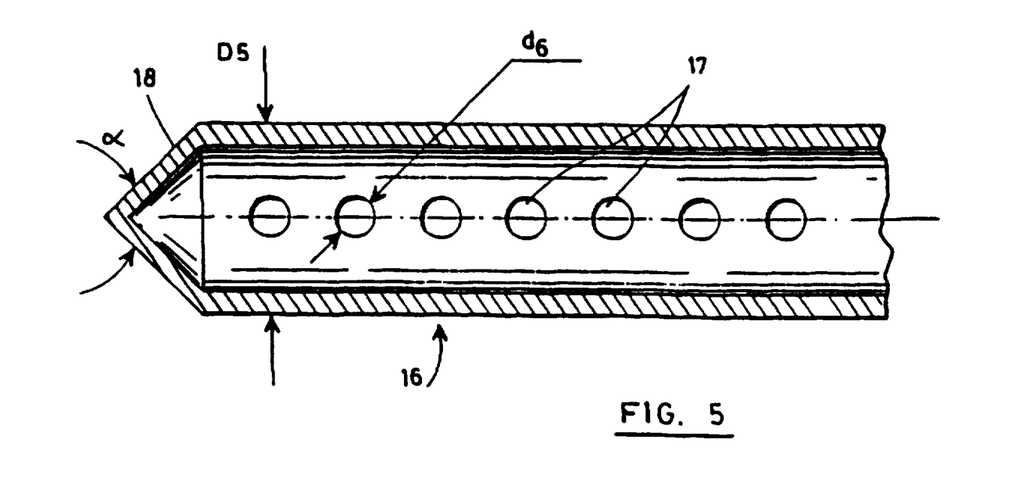
FIG. 5 is a cross-sectional view of the tip of the feeding pipe of the reactor of the apparatus shown in FIG. 2.

Means are further provided for radially feeding the olefin into the reactor 5. These means comprise a large feeding pipe 16 of diameter D5 that extends centrally and axially over a length $l_6$ within reactor. This feeding pipe 16 has a feeding end extending out of the reactor 5, which is connected to the pipeline 2-$a$. It also has a closed end 18 stopping at a short distance $l_7$ from the inlet of the reactor, and a plurality of radial openings 17 of diameter $d_6$ uniformly distributed along its length. As is better shown in FIG. 5, the closed end 18 of the olefin feeding pipe 16 is cone-shaped and has an apex of 45° to 60° facing the inlet of the reactor 5.

Advantageously, the diameters and lengths of the structural components of the tank 4 and reactor 5 are selected so that:

the ratio D1/D2 ranges from 9.5:1 and 24:1
the ratio D1/D6 ranges from 2:1 to 2.3:1, preferably 2:1
the ratio D1/D4 ranges from 1:2 to 1:4
the ratio D4/D5 ranges from 8:1 to 16:1
the ratio $l_1/l_2$ ranges from 3.3:1 to 5:1
the ratio $l_1/l_4$ ranges from 1.1:1 to 2.1:1
the ratio $l_1/l_5$ is ranging from 1:2 to 1:3
the ratio $l_5/l_6$ ranges from 1.1:1 to 1.3:1,
the ratio $l_7$ ranges from 2 to 6 times D5;
the ratio $l_3/D3$ ranges from 2:1 to 1:1; and
the ratio $d_6/D5$ ranges from 1:6 to 1:10.

Figure 4:
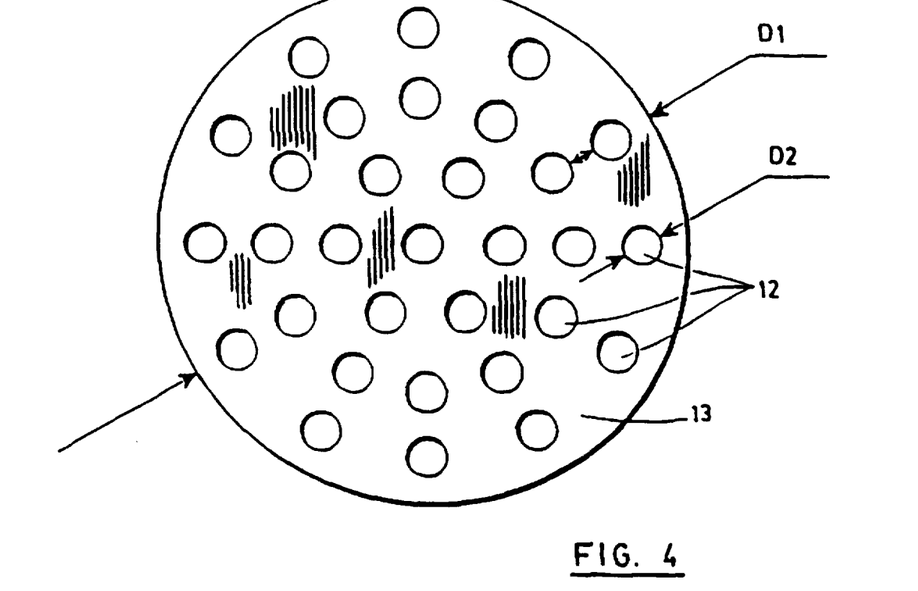
FIG. 4 is a top plan view of the perforated plate supporting the nozzles of the apparatus shown in FIG. 2.

Advantageously also, the sum of the cross-section areas of the nozzles 12 through which the isoparaffin is injected is equal to the cross-section area of the second branch pipe through which sulphuric acid is fed. Advantageously also, as shown in FIG. 4, the nozzles 12 are spaced apart from each other at a distance lower than twice their external diameter D2.

The apparatus shown in FIG. 2 is equipped with temperature probes 19, with samplers 20 and with a set of an acid analysis instruments 6 and 7 (see FIG. 1) consisting of an infrared spectrometer with a ATR (attenuated total reflexion) cell and a kinetic device for determination of the acidity function $H_o$.

This apparatus operates as follows.

The emulsion preparation tank 4 receives the isoparaffin via the pipeline 1-$a$ and sulphuric acid via the pipeline 3-$a$. The isoparaffin is finely dispersed and uniformly distributed within the tank 4 downstream the plate 13 by means of the nozzles 12. The emulsion of isoparaffin and sulphuric acid prepared within the tank 4 is fed to the reactor 5 through the branch pipe 14, where it is mixed with the olefin supplied to the reactor through the feeding pipe 16 which acts as a distributor and whose holes 17 are arranged to feed the olefin normally to the sulphuric acid-isoparaffin emulsion flow. As aforesaid, the closed end 18 of the feeding pipe 16 is cone-shaped to ensure uniform flow of the emulsion fed to the reactor 5.

The reactants get in contact in the reactor 5. Upon completion of the reaction, the reactants are discharged from the reactor 5 through the branch pipe 21.

As aforesaid, the isoparaffin sulphuric acid emulsion preparation tank 4 and the reactor 5 are equipped with temperature measuring devices 19 and with samplers 20. The produced heat is removed through adiabatic expansion as well as through the uniform distribution of reagents in the flow, which practically precludes local fluctuations of reagent concentrations and local overheatings.

The apparatus does not use any external cooling system thanks to the particular operation of the reactor in an isothermal mode. This is a major peculiarity and advantage of the invention. The apparatus does not comprise either any impeller or similar mixing apparatus to mix the reactants, thereby making it much easier to manufacture, maintain and operate.

TEST RESULTS

The apparatus disclosed hereinabove was actually experimented during a plurality of tests carried out for the sulphuric acid alkylation of olefins. The apparatus used during these tests had a total length of about 5 meters and included a reactor whose diameter D4 was equal to about 0.6 meter. The dimensions of the other structural components were varied during some of the tests for comparison purposes, as will be reported hereinafter.

All the tests were carried with the following raw materials:

catalyst: sulphuric acid having a concentration of 85–99% by weight;

isoparaffin: isobutane having a purity index of 40 to 80% by weight; and olefin: a butane-butylene fraction containing about 50% by weight of butylene (divided as follows: about 10 to 20% by weight of isobutylene; about 6 to 14% by weight of α-butylene and about 10 to 24% by weight of β-butylenes), together with about 4 to 5% by weight of isopentane and about 2% by weight of amylenes.

The sulphuric acid and isobutane were fed and mixed in the emulsion preparation tank 4 of the apparatus and the so-prepared emulsion was then fed to the reactor 5 as was explained above.

Sulphuric acid was fed into the sulphuric acid-isobutane emulsion preparation tank 4 at a temperature of 5° to 20° C. This feeding temperature was controlled during the process as a function of the variation of the acid viscosity.

The butane-butylene fraction was fed into the reactor 5 at a temperature from −10°0 to +5° C.

The reaction was controlled to keep the temperature within this reactor between 8° to 20° C. and the surplus pressure between 1 and 7.5 kg/cm$^2$. The volume ratio of sulphuric acid-to-hydrocarbons was kept most of the time between 0.3:1–0.5:1 and the ratio of isoparaffin-to-olefin was kept most of the time between 3:1–5:1.

TESTS 1 TO 7

To check the importance of the flow rates of the emulsion and of the reaction mixture, tests were carried out at various emulsion flow rates $V_1$, and various reaction mixture flow rate $V_2$.

During these tests, the isoparaffin-to-olefin volume ratio was about 4:1 and the sulphuric acid-to-hydrocarbons ratio was about 0.5:1. The results of these tests are reported in Table I below.

TABLE 1

| Test No. | Flow rate $V_1$ (m/s) | Flow rate $V_2$ (m/s) | Yield (% of the theoretical) | Octane number |
|---|---|---|---|---|
| 1 | 0.1 | 0.02 | 83.1 | 90.7 |
| 2 | 0.2 | 0.04 | 96.3 | 94.6 |
| 3 | 0.5 | 0.05 | 98.7 | 95.1 |
| 4 | 1.2 | 0.16 | 99.3 | 96.4 |
| 5 | 1.4 | 0.18 | 99.6 | 96.4 |
| 6 | 2.0 | 0.27 | 94.2 | 93.2 |
| 7 | 2.1 | 0.28 | 73.1 | 90.1 |

Note: In this Table and the following Tables, the octane numbers above 94.0 have been obtained by research method. Those under 94.0 have been obtained by motor method.

It is obvious from Table I that the yield of alkylate and its quality are drastically reduced at flow rates $V_1$ and $V_2$ below 0.2 and 0.04 m/s respectively and over 2.0 and 0.27 m/s, respectively.

TESTS 8 TO 19

To check the importance of the isoparaffin-to-olefin volume ratio and of the sulphuric acid-to-hydrocarbons volume ratio on the reaction, tests were carried out with the raw material fed at different ratios, while the emulsion flow rate $V_1$ and reaction mixture flow rate $V_2$ were kept constant and equal to about 1.2 m/s and about 0.16 m/s, respectively.

TABLE 2

| Test No. | Sulphuric acid to hydrocarbons ratio | Isoparaffin-to olefin ratio | Octane number | Yield (% of the theoretical) |
|---|---|---|---|---|
| 8 | 0.1:1 | 4:1 | 97.3 | 44.5 |
| 9 | 0.2:1 | 4:1 | 97.3 | 50.0 |
| 10 | 0.3:1 | 4:1 | 96.2 | 94.7 |
| 11 | 0.5:1 | 4:1 | 96.7 | 98.3 |
| 12 | 0.8:1 | 4:1 | 90.1 | 98.6 |
| 13 | 1:1 | 4:1 | 89.7 | 98.3 |
| 14 | 1.5:1 | 4:1 | 86.4 | 98.9 |
| 15 | 0.4:1 | 3:1 | 96.0 | 97.7 |
| 16 | 0.4:1 | 2:1 | 95.4 | 97.3 |
| 17 | 0.4:1 | 1:1 | 74.0 | 98.4 |
| 18 | 0.4:1 | 5:1 | 95.3 | 98.3 |
| 19 | 0.4:1 | 10:1 | 96.2 | 97.9 |

The results given in Table 2 above show that an increase in the acid-to-hydrocarbons ratio from 0.1:1 to 0.3:1 results in a noticeable increase in the alkylation qualitative yield. However, when this ratio exceeds 0.5:1, the quality of the alkylate (i.e. its octane number) is drastically reduced.

These tests also shown that when the isoparaffin-to-olefin ratio is below 2:1, the alkylate quality is drastically reduced. There is no upper limit for this ratio. However, the tests show that any increase in this ratio over 5:1 is economically inefficient as it does not bring any noticeable variation in the quality and quantity of produced alkylate.

TESTS NOS. 20 TO 29

To check the relationship between the acidity function $H_o$ expressed in water addition to raw acid ($H_o^{wat}$) and measured during the alkylation process ($H_o^{alk}$), the relationship between $H_o^{alk}$ and the octane number of the produced alkylate, the following tests were carried out under the same conditions as in test No. 4. The results of these tests are reported in Table 3.

TABLE 3

| Test No. | $H_o^{wat}$ | $H_o^{alk}$ | Octane number | Analytic concentration of $H_2SO_4$ obtained by titration (% by weight) |
|---|---|---|---|---|
| 20 | −10.42 | −10.42 | 93.0 | 98.5 |
| 21 | −10.27 | −10.60 | 95.1 | 98.0 |
| 22 | −9.88 | −10.42 | 96.1 | 96.0 |
| 23 | −9.59 | −10.19 | 97.0 | 94.0 |
| 24 | −9.33 | −10.12 | 96.3 | 92.0 |
| 25 | −9.08 | −9.96 | 94.7 | 90.0 |
| 26 | −8.60 | −9.77 | 94.1 | 87.0 |
| 27 | −8.29 | −9.68 | 93.8 | 85.0 |
| 28 | −7.84 | −9.58 | 91.7 | 82.0 |
| 29 | −7.52 | −9.45 | 90.6 | 80.0 |

Table 3 shows that sulphuric solutions having the same analytic concentration measured by titration, can have different values of acidity function $H_o$ depending on the water content in the acid phase.

Table 3 also shows that the dilution of the acid with water results in sharper variations in the values of $H_o^{wat}$ than of $H_o^{alk}$. This is a proof that determination of the analytic concentration of sulphuric acid by titration does not characterize objectively the catalyst acidity. As a matter of fact, the acidity function $H_o^{alk}$ measured during the process, characterizes the quality of the acid phase more accurately.

It was found that the acidity has a tendency to increase at the beginning of the process, during the adaptation of the catalyst. It has also been found that the best quality of alkylate corresponds to an acidity function $H_o$ of about −10.2.

TESTS NOS. 30 TO 39

Tests were also carried out to determine the variation of the concentrations of $H_2SO_4$ undissociated molecules during dilution of raw acid with water ($C^{wat}_{H_2SO_4}$) and during the alkylation process $C^{alk}_{H_2SO_4}$ and the variations of the octane number of the resulting alkylate versus the variation of $C^{alk}_{H_2SO_4}$. The results of these test are reported in Table 4.

TABLE 4

| Test No. | wat $C_{H_2SO_4}$ (g · mol./l) | alk $C_{H_2SO_4}$ (g · mol./l) | Octane number | Analytic concentration of $H_2SO_4$ obtained by titration (% by weight) |
|---|---|---|---|---|
| 30 | 16.9 | 16.9 | 93.0 | 98.5 |
| 31 | 16.8 | 16.4 | 95.1 | 98.0 |
| 32 | 13.9 | 15.2 | 96.1 | 96.0 |
| 33 | 11.4 | 14.4 | 97.0 | 94.0 |
| 34 | 9.0 | 13.1 | 96.3 | 92.0 |
| 35 | 6.8 | 11.3 | 94.7 | 90.0 |
| 36 | 4.2 | 9.2 | 94.1 | 87.0 |
| 37 | 3.0 | 8.1 | 93.8 | 85.0 |
| 38 | 1.4 | 6.8 | 91.7 | 82.0 |
| 39 | 0.75 | 5.7 | 90.6 | 80.0 |

Table 4 shows that the dilution of sulphuric acid with water results in sharper decrease in the concentration of $H_2SO_4$ undissociated molecules than its dilution in the alkylation process.

Table 4 also shows that a decrease in the concentration $C^{alk}_{H_2SO_4}$ from 16.9 to 14.4 g.mol./l improves the alkylated gasoline quality. This can be attributed to the accumulation of bisulphates and organic components in the acid phase. However, a further decrease in the concentration $C^{alk}_{H_2SO_4}$ results in the impairment of the product quality. Bearing in mind that the addition of promoters to the acid phase disturbs the balance of sulphuric acid dissociation, the above tests shown that proper control of the variation of concentration of $H_2SO_4$ undissociated molecules makes it possible to effectively control the optimal composition of the catalyst.

TESTS NOS. 40 TO 82

Tests were carried out to check the importance that may have the geometrical dimensions of the different structural components of the apparatus according to the invention on the product yield and quality. These tests were carried out under the same condition as in test No. 4. The results of these tests are reported in Tables 5 to 7.

TABLE 5

| Test No. | D1/D2 | D1/D4 | D1/D6 | D4/D5 | Octane number | Yield (% of theoretical) |
|---|---|---|---|---|---|---|
| 40 | 9.5:1 | 1:1 | 2:1 | 8:1 | 98.7 | 60.3 |
| 41 | 9.5:1 | 1:2 | 2:1 | 8:1 | 97.3 | 98.6 |
| 42 | 9.5:1 | 1:4 | 2:1 | 8:1 | 96.2 | 99.1 |
| 43 | 9.5:1 | 1:6 | 2:1 | 8:1 | 90.7 | 98.4 |
| 44 | 7.1:1 | 1:2 | 2:1 | 8:1 | 87.3 | 90.1 |
| 45 | 14.3:1 | 1:2 | 2:1 | 8:1 | 96.2 | 98.4 |
| 46 | 23.8:1 | 1:2 | 2:1 | 8:1 | 95.8 | 98.1 |
| 47 | 28.6:1 | 1:2 | 2:1 | 8:1 | 95.3 | 84.7 |
| 48 | 9.5:1 | 1:2 | 1:1 | 8:1 | 87.3 | 91.7 |
| 49 | 9.5:1 | 1:2 | 4:1 | 8:1 | 88.9 | 92.6 |
| 50 | 9.5:1 | 1:2 | 2:1 | 6:1 | 97.1 | 86.2 |
| 51 | 9.5:1 | 1:2 | 2:1 | 12:1 | 96.5 | 97.2 |
| 52 | 9.5:1 | 1:2 | 2:1 | 16:1 | 94.9 | 97.1 |
| 53 | 9.5:1 | 1:2 | 2:1 | 20:1 | 90.1 | 84.6 |

Table 5 shows that the best product quality and yield are achieved when the ratio D1/D2 is ranging from 9.5:1 to 23.8:1; the ratio D1/D4 from 1:2 to 1:4; the ratio D1/D6 is equal to about 2:1 and the ratio D4/D5 is ranging from 8:1 to 16:1.

TABLE 6

| Test No. | $l_1/l_5$ | $l_1/l_2$ | $l_1/l_4$ | $l_3/D3$ | $l_5/l_6$ | $l_7/D5$ | Octane Number | Yield (% of the theoretical) |
|---|---|---|---|---|---|---|---|---|
| 54 | 1:1 | 3.3:1 | 1.4:1 | 1:1 | 1.3:1 | 4 | 93.7 | 84.1 |
| 55 | 1:2 | 3.3:1 | 1.4:1 | 1:1 | 1.3:1 | 4 | 94.2 | 96.2 |
| 56 | 1:3 | 3.3:1 | 1.4:1 | 1:1 | 1.3:1 | 4 | 95.2 | 98.4 |
| 57 | 1:4 | 3.3:1 | 1.4:1 | 1:1 | 1.3:1 | 4 | 80.6 | 98.2 |
| 58 | 1:3 | 1.7:1 | 1.4:1 | 1:1 | 1.3:1 | 4 | 74.2 | 96.3 |
| 59 | 1:3 | 5.0:1 | 1.4:1 | 1:1 | 1.3:1 | 4 | 96.3 | 98.2 |
| 60 | 1:3 | 6.7:1 | 1.4:1 | 1:1 | 1.3:1 | 4 | 86.3 | 94.2 |
| 61 | 1:3 | 3.3:1 | 0.7:1 | 1:1 | 1.3:1 | 4 | 81.9 | 92.6 |
| 62 | 1:3 | 3.3:1 | 1.1:1 | 1:1 | 1.3:1 | 4 | 96.1 | 98.2 |
| 63 | 1:3 | 3.3:1 | 1.4:1 | 1:1 | 1.3:1 | 4 | 94.7 | 96.3 |
| 64 | 1:3 | 3.3:1 | 2.1:1 | 1:1 | 1.3:1 | 4 | 95.1 | 97.7 |
| 65 | 1:3 | 3.3:1 | 2.5:1 | 1:1 | 1.3:1 | 4 | 90.3 | 87.4 |
| 66 | 1:3 | 3.3:1 | 1.4:1 | 0.5:1 | 1.3:1 | 4 | 87.6 | 96.3 |
| 67 | 1:3 | 3.3:1 | 1.4:1 | 2:1 | 1.3:1 | 4 | 94.6 | 96.8 |
| 68 | 1:3 | 3.3:1 | 1.4:1 | 3:1 | 1.3:1 | 4 | 90.1 | 89.3 |
| 69 | 1:3 | 3.3:1 | 1.4:1 | 3:1 | 0.7:1 | 4 | 93.1 | 84.7 |
| 70 | 1:3 | 3.3:1 | 1.4:1 | 3:1 | 1.0:1 | 4 | 94.2 | 97.3 |
| 71 | 1:3 | 3.3:1 | 1.4:1 | 3:1 | 1.7:1 | 4 | 91.7 | 81.3 |
| 72 | 1:3 | 3.3:1 | 1.4:1 | 3:1 | 1.3:1 | 1 | 70.4 | 89.3 |
| 73 | 1:3 | 3.3:1 | 1.4:1 | 3:1 | 1.3:1 | 2 | 94.7 | 98.3 |
| 74 | 1:3 | 3.3:1 | 1.4:1 | 3:1 | 1.3:1 | 3 | 95.1 | 98.1 |
| 75 | 1:3 | 3.3:1 | 1.4:1 | 3:1 | 1.3:1 | 5 | 94.7 | 98.3 |
| 76 | 1:3 | 3.3:1 | 1.4:1 | 3:1 | 1.3:1 | 6 | 95.1 | 98.4 |
| 77 | 1:3 | 3.3:1 | 1.4:1 | 3:1 | 1.3:1 | 7 | 84.6 | 98.2 |

Table 6 shows that the best product quality and yield are achieved when the ratio $l_1/l_5$ is ranging from 1:2 to 1:3, $l_1/l_2$ from 3.3:1 to 5:1; $l_1/l_4$ from 1.1:1 to 2.1:1; $l_3/D3$ from 2:1 to 1:1; $l_5/l_6$ from 1:1 to 1.3:1; and $l_7$ is ranging from 2D5 to 6D5.

TABLE 7

| Test No. | α (o) | Octane number | Yield (% of the theoretical) |
|---|---|---|---|
| 78 | 30 | 95.3 | 86.3 |
| 79 | 40 | 95.7 | 86.7 |
| 80 | 45 | 95.4 | 98.3 |
| 81 | 60 | 94.7 | 97.1 |
| 82 | 90 | 72.1 | 84.7 |

Table 7 shows the best product yield and quality is achieved with the angle α of the cone-shaped end of the olefin feeding pipe is ranging from 45° to 60°.

TESTS NOS. 83 TO 86

Tests were further carried out under the same conditions (flow rates, and ratios) as test No. 4 to determine the relationship between the temperature of the sulphuric acid fed into the tank and the quality of the alkylate. During these tests the initial concentration of sulphuric acid was 95% by weight. The results of these tests are reported in Table 8.

TABLE 8

| Test No. | Acid temperature °C. | Octane number | Yield (% of the theoretical) |
|---|---|---|---|
| 83 | 0 | 94.6 | 97.6 |
| 84 | 10 | 95.3 | 97.8 |
| 85 | 20 | 95.6 | 98.4 |
| 86+ | 25 | 61.3 | 98.6 |

+ denotes heavy resinification

Table 8 shows that the acid initial temperature affects the quality of the resulting product. It also shows that an increase in temperature over 20° C. sharply intensifies secondary resinification reaction, which results in a reduction of product quality. Eventhough, in the above tests, a good result was obtained at 0° C. because the acid concentration was 95%, it is important that the temperature of the acid be not lower than 5° C. to make the process useful within the full range of acid concentration.

TEST NO. 87

A test was carried out to determine the fractional composition of an alkylate having an octane number (motor method) of 94.3. This alkylate is produced with a 93% sulphuric acid solution. The results of this test are reported in Table 9.

TABLE 9

| Temperature °C. | Boiling (%) | Temperature °C. | Boiling (%) |
|---|---|---|---|
| 61 | 10 | 116 | 60 |
| 98 | 20 | 118 | 70 |
| 108 | 30 | 123 | 80 |
| 109 | 40 | 131 | 90 |
| 111 | 50 | 158 (b.p.) | — |

We claim:

1. A process for the sulphuric acid alkylation of at least one olefin with at least one isoparaffin, said process comprising the steps of:

a) feeding sulphuric acid into an emulsion preparation zone having a longitudinal axis;

b) injecting said at least one isoparaffin through a plurality of nozzles that extend into said emulsion preparation zone in a direction generally parallel to said longitudinal axis, in order to form a homogeneous emulsion of said at least one isoparaffin within said sulphuric acid within said emulsion preparation zone;

c) feeding the so-prepared emulsion into a separate reaction zone from said emulsion preparation zone, and injecting said at least one olefin into the so-prepared emulsion in said reaction zone in a generally radial direction relative to said longitudinal axis, whereby a reaction mixture is formed;

d) allowing said reaction mixture to react within said reaction zone and;

e) recovering from said reaction zone the so-reacted mixture.

2. The process of claim 1, comprising the additional steps of:

f) controlling steps (a) and (b) so that the emulsion moves within the emulsion preparation zone at a flow rate of 0.2 to 2 m/s.

g) controlling step (c) so that the reaction mixture that is formed after injection of said at least one olefin moves within the reaction zone at a flow rate of 0.04 to 0.27 m/s.

3. The process of claim 2, wherein:

in step (c), the injection of said at least one olefin is carried out at a plurality of points and in directions perpendicular to the flow of said emulsion.

4. The process of claim 3, comprising the additional steps of:

h) controlling step (a) so that the volume ratio of sulphuric acid to hydrocarbons present within the reaction zone ranges from 0.3 to 0.5:1; and i) simultaneously controlling steps (b) and (c) so that the volume ratio of said at least one isoparaffin to said at least one olefin is higher than 2:1.

5. The process of claim 4, wherein:

in step (a), said at least one isoparaffin is isobutane; said isobutane is fed at a temperature ranging from $-10°$ to $5°$ C.; and said sulphuric acid is fed at a temperature ranging from $5°$ to $20°$ C.;

in step (c), said at least one olefin is injected at a temperature ranging from $-10°$ to $5°$ C.; and in said emulsion preparation and reaction zones, the pressure is held between 1 and 7.5 surplus atmospheres.

6. The process of claim 4, comprising the additional step of:

j) measuring the acidity function $H_o$ of the sulphuric acid within both the emulsion preparation zone and the reaction zone and controlling the quality of the sulphuric acid fed in step (a) and the temperature and pressure of the sulphuric acid, of the at least one isoparaffin and of the at least one olefin fed or injected in steps (a), (b) and (c) so that said acidity function $H_o$ ranges from $-10.6$ to $-9.5$.

7. The process of claim 5, comprising the additional step of:

k) measuring the concentration of undissociated sulphuric acid molecules within both the emulsion preparation zone and the reaction zone and controlling the quality of the sulphuric acid fed in step (a) and the temperature and pressure of the sulphuric acid, of the at least one isoparaffin and of the at least one olefin fed or injected in steps (a), (b) and (c) so that said concentration ranges from 6.8 to 16.9 mol/l.

8. The process of claim 1, wherein said reaction zone is coaxial to said emulsion preparation zone.

\* \* \* \* \*